(12) United States Patent
Proctor, Jr. et al.

(10) Patent No.: US 10,821,030 B2
(45) Date of Patent: Nov. 3, 2020

(54) APPARATUS AND METHOD FOR A TEMPERATURE RELEASED ADHESIVE STRUCTURE FOR USE WITH BANDAGES

(71) Applicant: Genesis Medical Devices LLC, Indialantic, FL (US)

(72) Inventors: James A. Proctor, Jr., Indialantic, FL (US); Daniel N. Segina, Satellite Beach, FL (US)

(73) Assignee: Genesis Medical Devices LLC, Indialantic, FL (US)

( * ) Notice: Subject to any disclaimer, the term of this patent is extended or adjusted under 35 U.S.C. 154(b) by 612 days.

(21) Appl. No.: 15/438,911

(22) Filed: Feb. 22, 2017

(65) Prior Publication Data

US 2017/0240777 A1 Aug. 24, 2017

Related U.S. Application Data

(60) Provisional application No. 62/299,283, filed on Feb. 24, 2016.

(51) Int. Cl.
| | |
|---|---|
| *A61L 15/58* | (2006.01) |
| *A61F 13/00* | (2006.01) |
| *C09J 7/26* | (2018.01) |
| *C09J 133/26* | (2006.01) |
| *C09J 133/10* | (2006.01) |
| *C09J 133/12* | (2006.01) |
| *C09J 133/18* | (2006.01) |
| *C09J 135/04* | (2006.01) |
| *A61F 13/02* | (2006.01) |

(52) U.S. Cl.
CPC ...... *A61F 13/0253* (2013.01); *A61F 13/0256* (2013.01); *A61F 13/0259* (2013.01); *A61F 13/0269* (2013.01); *A61L 15/58* (2013.01); *C09J 7/26* (2018.01); *C09J 133/10* (2013.01); *C09J 133/12* (2013.01); *C09J 133/18* (2013.01); *C09J 133/26* (2013.01); *C09J 135/04* (2013.01); *C09J 2201/16* (2013.01); *C09J 2423/006* (2013.01); *C09J 2433/00* (2013.01); *C09J 2433/006* (2013.01); *C09J 2475/006* (2013.01)

(58) Field of Classification Search
None
See application file for complete search history.

(56) References Cited

U.S. PATENT DOCUMENTS

| | | | |
|---|---|---|---|
| 4,324,595 | A | 4/1982 | Kasprzak |
| 5,156,911 | A | 10/1992 | Stewart |
| 7,078,582 | B2 | 7/2006 | Stebbings et al. |
| 7,396,976 | B2 | 7/2008 | Hurwitz et al. |
| 2013/0123678 | A1 | 5/2013 | Carty et al. |

*Primary Examiner* — Frank D Ducheneaux
(74) *Attorney, Agent, or Firm* — VLP Law Group, LLP; David J. Thibodeau, Jr.

(57) ABSTRACT

An adhesive article that remains securely bonded to a substrate until a stimuli is applied. The article may be embodied as an adhesive tape, a bandage, or as other articles. The stimuli may be a change in temperature or application of a reduction that causes a structure within the article to break, creak, or otherwise disrupt to expose the adhesive to a solvent, such as via a difference in Coefficient of Thermal Expansion (CTE) or by exposing the article to a glass transition temperature.

28 Claims, 14 Drawing Sheets

APPARATUS AND METHOD FOR A TEMPERATURE RELEASED ADHESIVE STRUCTURE FOR USE WITH BANDAGES

CROSS-REFERENCE TO RELATED APPLICATION(S)

This application claims priority to U.S. Provisional Application No. 62/299,283, filed on Feb. 24, 2016. The entire teachings of the above application is incorporated herein by reference.

BACKGROUND

Technical Field

This application relates to adhesive articles, which may include adhesive tapes, bandages, and other items.

Background Information

U.S. Pat. No. 5,156,911 describes a bandage having an adhesive that is activated upon exposure to a specific temperature, such as a typical human body temperature.

U.S. Pat. No. 7,078,582 describes articles designed to adhere to the skin or other delicate surfaces that use a stretch-removable pressure sensitive adhesive. The articles delaminate when physically stretched.

Adhesive bandages are known that can be removed via application of pressure. U.S. Pat. No. 7,396,976 describes one such bandage that contains pockets or microcapsules filled with an ingredient that inactivates an adhesive. The pockets or microcapsules are ruptured by applying pressure to the bandage.

SUMMARY

The use of temperature sensitive adhesives that change state depending on body temperature are not ideal for use on bandages.

Pressure-releasable and stretch-releasable bandages also have shortcomings. For example, they may be released inadvertently such as when a patient touches the bandage, rolls over in their sleep, inadvertently bumps into an object, or exposes the bandage to physical stress.

What is needed is a way to securely attach a bandage or other object with an aggressive adhesive that only becomes releasable upon exposure to a stimuli other than directly applied pressure, in many applications.

In general, an adhesive article is engineered to remain securely bonded to a substrate until a stimuli is applied. The article may be embodied as an adhesive tape, a bandage, or as other articles. The stimuli may be a change in temperature (induced by a compressed air canister as one example) or application of radiation (microwaves, or ultrasonic emissions as examples) that causes a structure within the article to break, crack, or otherwise disrupt. The disruption in the structure exposes the adhesive to a solvent. The disruption can be caused via a difference in Coefficient of Thermal Expansion (CTE), by exposing one or more material layers to a glass transition temperature, or in other ways, and in some cases combinations of approaches.

More particularly, a stimuli-responsive adhesive article may be formed from an adhesive, a polymer or other material defining an enclosed cavity, and a solvent disposed within the cavity. The article is made responsive to a stimuli, the stimuli comprising at least one of radiation or temperature change, such that upon application of the stimuli, the adhesive article is disrupted, causing the solvent to react with the adhesive, making the article removable.

The encapsulating material may preferably be, in whole or in part, insoluble in the solvent, in particular within any planned temperate range for which the solvent should not be released. The adhesive may preferably be soluble or swellable in the solvent. In one embodiment, the encapsulating material may become soluable, or otherwise weakened at temperatures in which the solvent is intended to excape the encapsulation.

In one embodiment, the material may include a second polymer disposed adjacent a first polymer, and the two polymers have different coefficients of thermal expansion.

The polymer may be implemented as a layer of material, or as a spherical structure.

The stimuli may be cooling, heating, ultrasonic frequency, radio frequency, and/or microwave frequency radiation as non-limiting examples.

The material layers may define a plurality of pockets, linearly aligned or aligned in a grid, or in another geometric arrangement.

To encourage conduction of the stimuli, one or more channels may be provided within or adjacent the article. The channels can have defined shapes or constructions to encourage further action by the simulu, such as by feeding air into an expansion space in communication with one or more of the channels, to expand and further cool the air.

A glass transition temperature and/or coefficient of thermal expansion of the materials may be selected to encourage disrtuption of the structure upon application of the stimuli.

In some embodiments, the adhesive is formed of a material selected from the group consisting of: C1-12 alkyl acrylate, C1-12 alkyl cyanoacrylate, C1-12 alkyl methacrylate, C1-12 alkyl acrylamide, C1-12 alkyl methacrylamide, vinyl ether, vinyl ester, siloxane, hydrogel, hydrocolloid, silicone, silicone gel, and a combination thereof.

In some embodiments, the material is methyl 2-cyanoacrylate, ethyl-2-cyanoacrylate, n-butyl cyanoacrylate, or 2-octyl cyanoacrylate.

The solvent may be a ketone-based solvent, an alcohol-based solvent, or an ester-based solvent, methyl ethyl ketone, isopropanol, ethanol, ethyl acetate, or tetrahydrofurfuryl acetate.

In other embodiments, the polymer is polypropylene, polymethylpentene, poly(3-hydroxybutyrate-co-3-hydroxyvalerate), polyvinylidene chloride, polyethylene, ethylene vinyl alcohol, poly(methyl methacrylate), and/or polyurethane, or polymethylpentene, or poly(3-hydroxybutyrate-co-3-hydroxyvalerate).

BRIEF DESCRIPTION OF THE DRAWINGS

The description below refers to the accompanying drawings, of which.

DETAILED DESCRIPTION OF ILLUSTRATIVE EMBODIMENT(S)

Figure 1A:
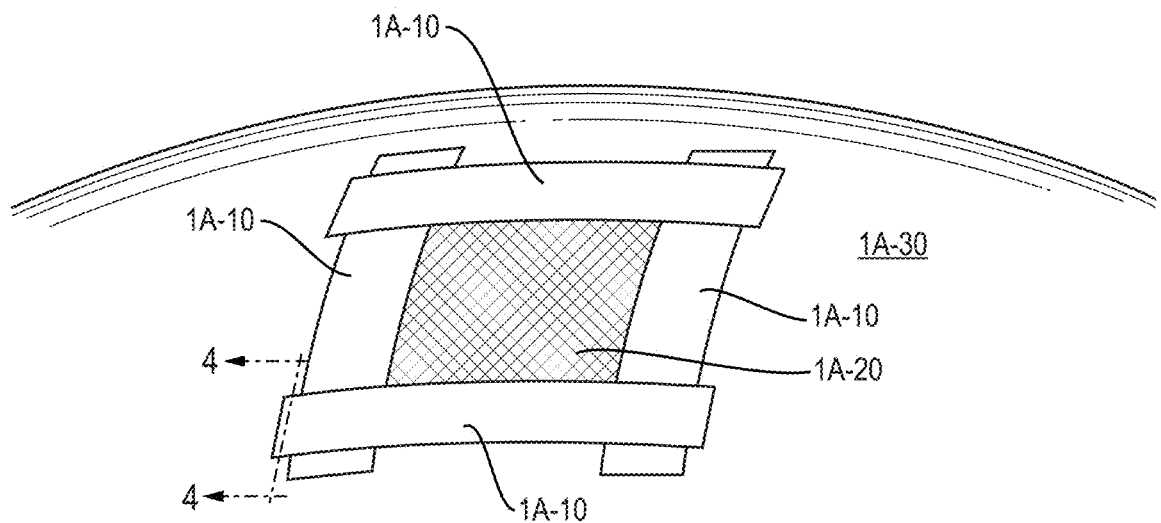
FIG. 1A illustrates a wound dressing using an adhesive tape constructed according to one embodiment.

FIG. 1A shows an adhesive tape constructed in accordance with the teachings herein. Sections or strips 1A-10 of the adhesive tape are placed around the periphery of a wound dressing, such as a non-sticky, sterile gauze pad 1A-20. The tape sections 1A-10 adhere to the skin 1A-30 of a patient and hold the dressing in place. Other embodiments are possible. For example, dressing 1A-20 could be just a cotton gauze, or it could be an engineered dressing such as a back-sealed structure providing a hermetic seal.

Figure 1B:
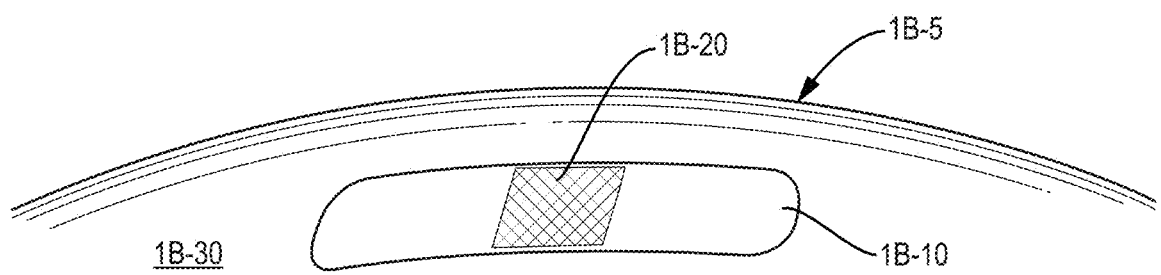
FIG. 1B is another implementation of a wound dressing.

FIG. 1B is another implementation as an adhesive bandage 1B-5 in a form that is often referred to by now generalized trademark "Band-Aid" in the U.S. or "Elastoplast" in other countries. The bandage 1B-5 includes a flexible adhesive backing 1B-10 and a strip of gauze 1B-20 underneath it, located between the adhesive backing 1B-10 and the patient's skin 1B-30.

Figure 2A:
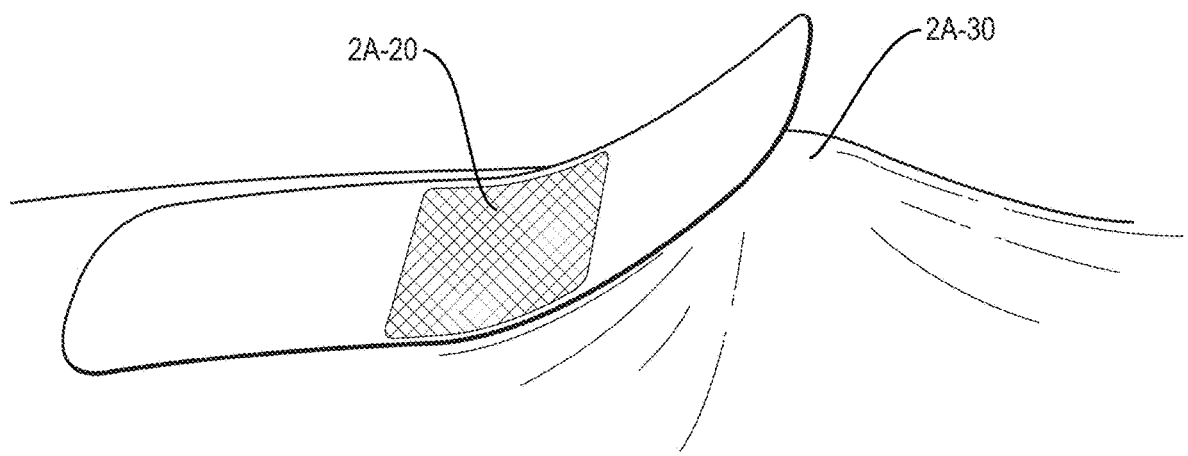
FIGS. 2A and 2B show how a prior art bandage causes pain and/or anxiety when removed.

FIG. 2A illustrates what often happens when attempting to remove a prior art bandage from the skin 2A-30. The adhesive sections 2A-20 may aggressively adhere to, or pull on the skin.

Figure 2B:
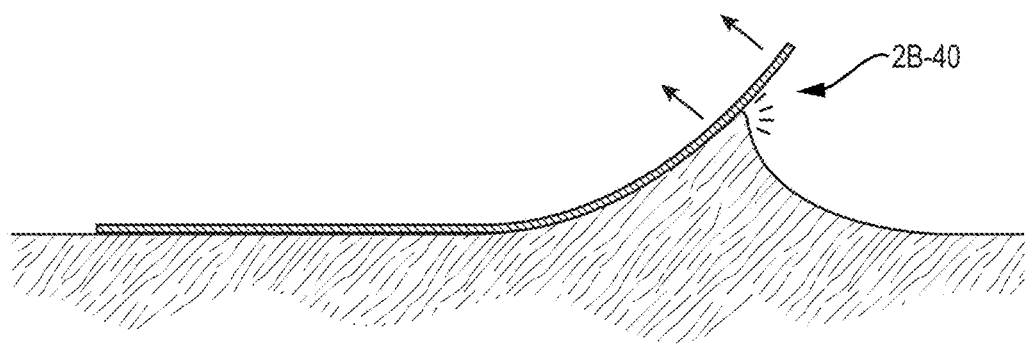

Sometimes, for elderly people or people with a sensitive epidermal condition, the skin can actually be torn away, as shown at point 2B-40 in FIG. 2B. This phenomenon also causes anxiety among children. Also, patients with a very serious wound or recovering from surgery may have left the bandage in place for an extended period of time, causing the adhesive to become more difficult to remove. Even if the adhesive will only pull on, and not tear the skin, there is much anxiety about the upcoming bandage removal.

In reality, it would actually be preferable if an even more aggressive adhesive could be used than is typical for a band-aid or medical tape. A stronger adhesive would lead to fewer incidents of a bandage falling off prematurely, or upon exposure to water, or other ambiment environmental conditions.

Tape sections 1A-10 may be used in non-medical applications, indeed just about anywhere adhesive tape is found to be useful, but where removal of tape having an aggressive adhesive might otherwise be problematic.

Figure 3:
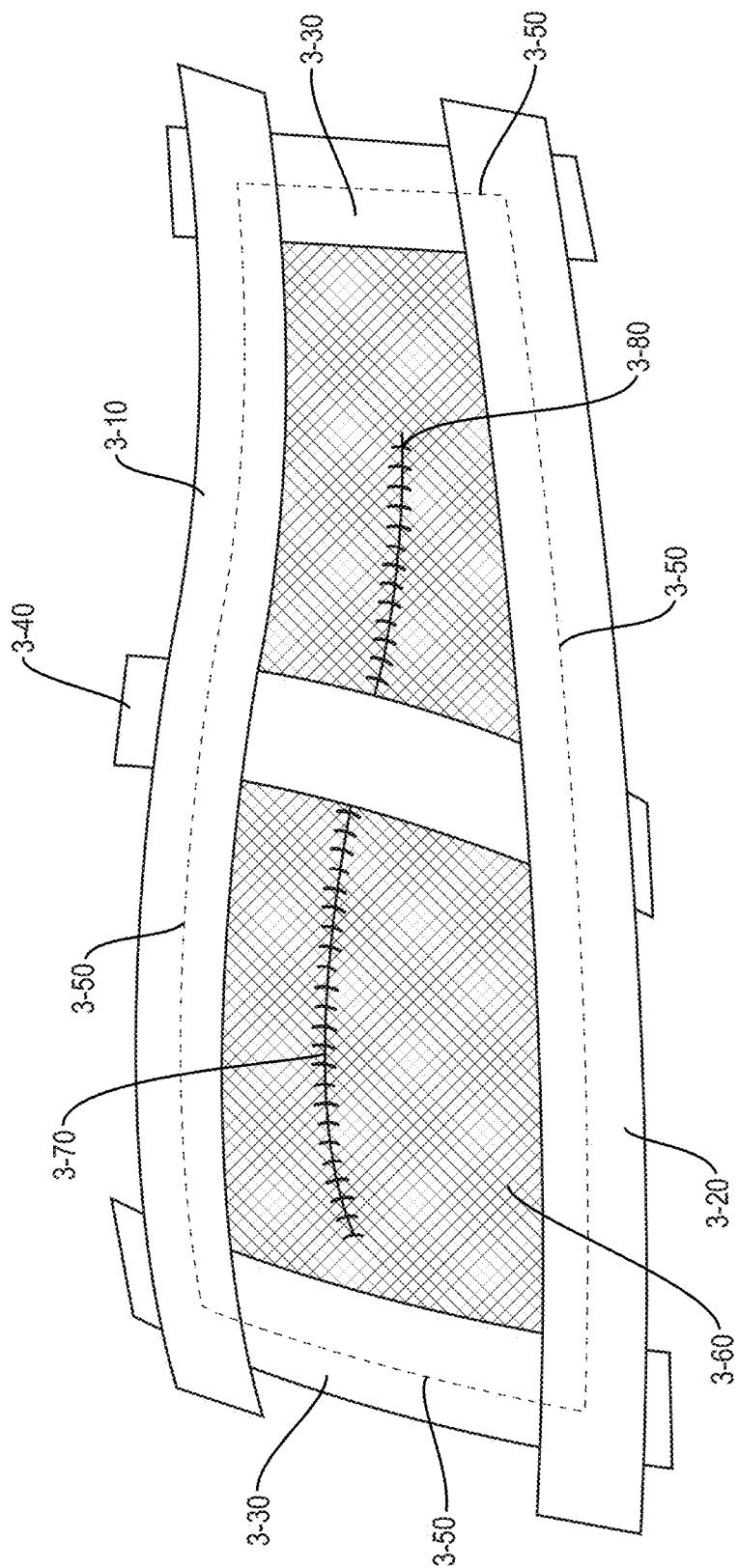
FIG. 3 is another embodiment using adhesive tape sections.

FIG. 3 is another embodiment using adhesive tape sections 3-10, 3-20, 3-30 and 3-40 to cover an incision post-surgery. A gauze pad or other dressing 3-60 has edges 3-50 (indicated by the dotted line) and covers the incision 3-70. Incision 3-70 may include stitches or staples 3-80. In some embodiments, the dressing 3-60 is a cellophane-like plastic for use in Negative Pressure Wound Therapy (NPWT) applications. NPWT can be used to promote healing by subjecting the incision 3-70 to negative pressure to cause a drawing of fresh blood to the surface.

Some of the adhesive strips, such as 3-10 and 3-20 may overlap other adhesive strips 3-30. Note adhesive tape 3-40 just happens to be across the middle of the wound area (that is, tape 3-40 lays completely on top of the gauze 30-80). The use of stiff adhesives on tape section 3-40, described below, may assist with stabilizing the dressing.

Figure 4:
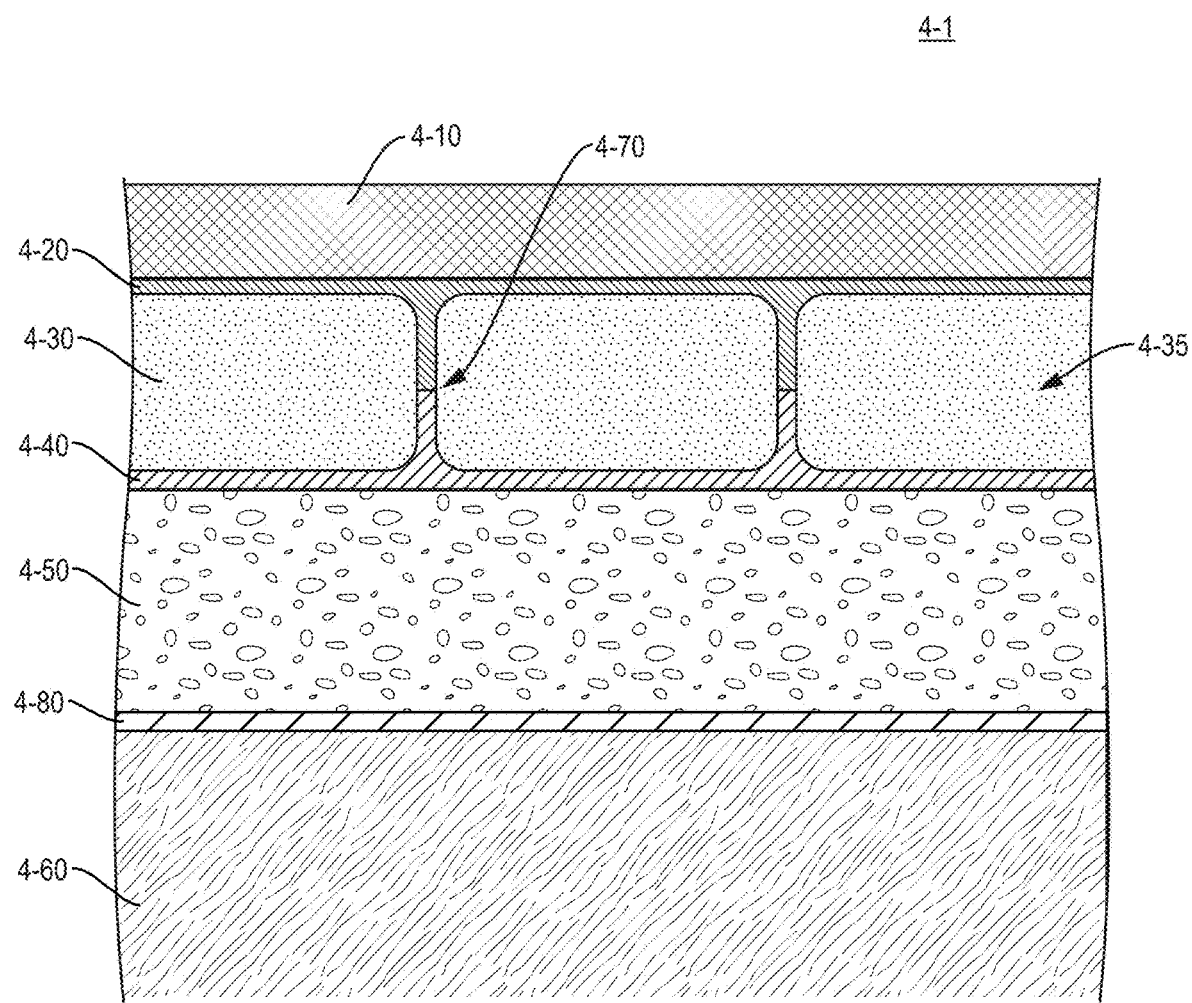
FIG. 4 is a cross-sectional view taken along the dotted line 4-4 of FIG. 1A.

FIG. 4 is a cross sectional view showing an adhesive tape embodiment 4-1 in more detail. The view is taken across dotted lines 4-4 of FIG. 1A. Here, a flexible backing layer 4-10 contacts a first layer 4-20. The backing 4-10 can be any suitable flexible material, such as a polymer used in medical bandages. Backing 4-10 may be the same as and integrated with first layer 4-20 or it may be a different layer. First layer 4-20 may be formed from one or more of the polymers discussed below in detail, or some other material. In some embodiments, the first layer may be coated with a metal foil, contain metal particles, or even be entirely metal or some other thermally conductive material.

A second optional polymer layer 4-40 is disposed adjacent at least some portions of first polymer layer 4-20. Layers 4-20, 4-40 may have different Coefficients of Thermal Expansion (CTE) in some embodiments. In one case, the bottom layer 4-40 might be thermoresistive or reactive and the top layer 4-20 is not.

A solvent 4-30 is encapsulated between layers 4-20, 4-40. In other words, layers 4-20, 4-40 define one or more cavities or pockets 4-35 into which solvent 4-30 is placed.

Adhesive 4-50 is disposed in the bottom of polymer layer 4-40. Item 4-60 is the patient's flesh or other surface under adhesive 4-50 to which the tape has been adhered.

There might optionally be some protective layer 4-80 placed on the adhesive 4-50 during manufacture, which is then removed before the tape is applied to the skin or other surface. The protective layer 4-80, if present, protects the adhesive 4-50 and prevents adhesive 4-50 from curing prior to application; it is typically easily removed from adhesive 4-50 as is known for prior art Band-Aids.

Joint(s) 4-70 may be formed between the two dissimilar layers 4-20, 4-40 in one embodiment. It is this joint, or interface, that disrupts upon application of an external stimuli. In an embodiment where the layers 4-20, 4-40 have different CTEs, the stimuli might be a cold fluid such as air. The amount of the force associated with a difference in CTE's will depend on the thickness of the layers, the dimensions of the pockets, and the materials. The force between the materials having different CTEs should be sufficient to break the joint(s) 4-70 when the stimuli is applied.

In other embodiments, described below, not all of the cavities 4-35 between layers 4-20, 4-40 may have encapsulated solvent 4-30. These empty cavities might be perforations open to the adhesive 4-50 that tear at the joint 4-70, thus allowing solvent 4-30 to flow toward the adhesive.

As an alternative and/in addition to the implementations described above, the bottom polymer layer 4-40 may have a relatively low glass transition temperature, such as 0° C. or even lower. Upon application of a cold fluid (such as cold air) to the article, the layer 4-40 may crack to then release solvent 4-30 onto the adhesive.

Whether by way of having different CTEs of layers 4-20, 4-40 cause a mechanical pulling of the top polymer 4-20 relative to the bottom polymer 4-40, or by having a selected glass transition temperature, or some combination of these effects, the bandage 4-1 is released as the solvent 4-30 comes in contact, through such rupturings, with the adhesive 4-50.

Figure 5A:
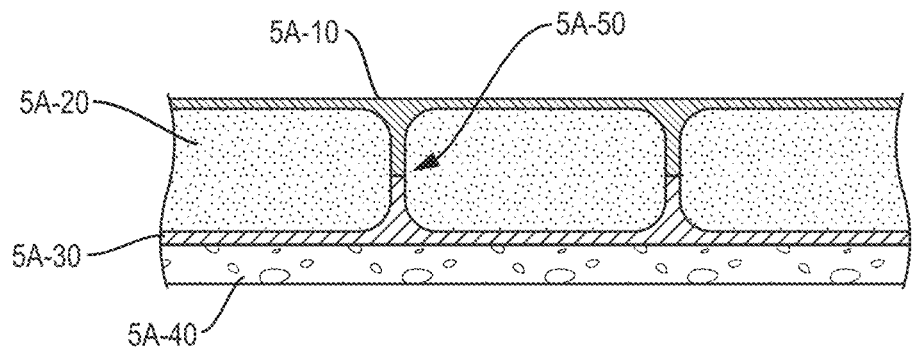
FIG. 5A shows an embodiment without a separate backing layer.
Figure 5B:
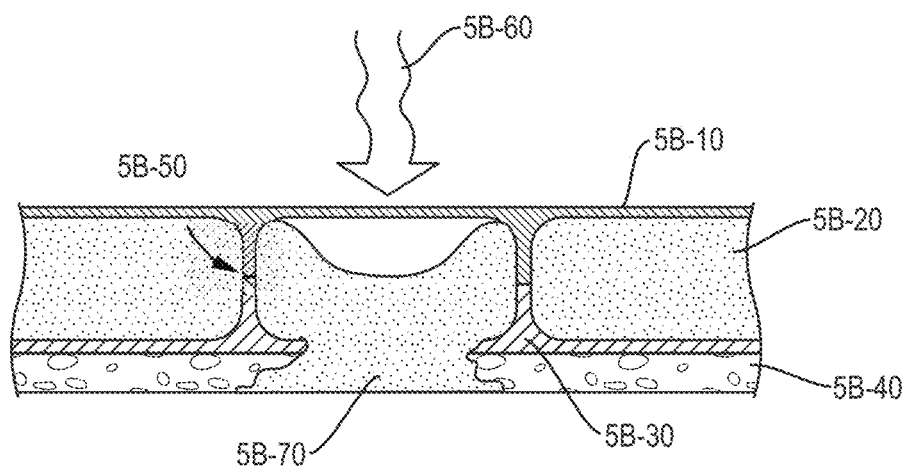
FIG. 5B illustrates the result when a stimuli is applied to the FIG. 5A embodiment.

FIG. 5A is an embodiment without a separate backing layer. This embodiment has a top polymer layer 5A-10, bottom polymer layer 5A-30, joint interface 5A-50, encapsulated solvent 5A-20, and adhesive 5A-40. The stimuli—such as cold air—causes a rupture of joint 5A-50 as in the FIG. 4 embodiment. FIG. 5B illustrates what happens after the stimuli is applied. Some breakage of the bottom layer 5B-30 has occurred, allowing the solvent 5B-70 to reach the adhesive 5B-40. This breakage could be as a result of a further stimuli, such as by applying a physical or mechanical force 5B-60 to the joint 5B-50, between the two polymers 5B-10, 5B-30.

In some embodiments, stimuli 5B-60 can be cold air causing the two polymers 5B-10, 5B-30 to separate due to their different CTEs. However, in other embodiments using other materials for 5B-10 and/or 5B-30 (as discussed below) the stimuli may be radiation, such as ultrasonic, radio-frequency (RF) or microwave frequency energy.

In most embodiments, it may be desirable for the solvent 5B-70 to not reach the lower polymer layer 5A-30 over a range of temperatures. However, thermoreactive polymers may be used, where polymer 5A-30 becomes susceptible at certain temperatures to then expose solvent 5A-20 (FIG. 5A) or 5B-70 (FIG. 5B). For example, a stimulus of cold air or warm are might cause the lower polymer 5B-30 to become weakened, releasing solvent onto the adhesive. In some embodiments, an expanding material (such as a polymer layer) may close an otherwise open aperture in a solvent chamber, above a specific temperature, and allow solvent to escape the chamber below a specific temperature range as a result of the contraction of the material(s) forming the aperture.

Figure 6:
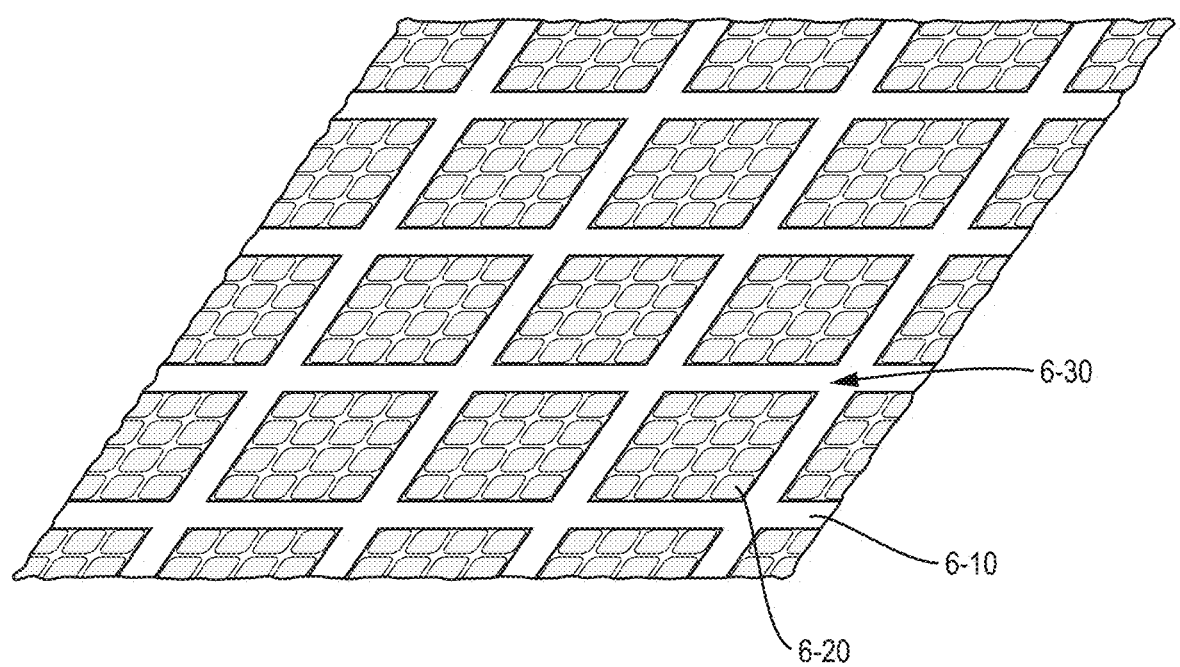
FIG. 6 shows multiple sets of encapsulated solvent pockets.

FIG. 6 depicts an embodiment with multiple sets of cavities or pockets that encapsulate solvent. An individual encapsulated solvent pocket 6-20 is part of a 4 by 4 set 6-30 of pockets 6-20 (the set being identified by the heavy black line 6-30). Two or more sets 6-30 may be arranged in a larger grid defined by one or more channels 6-10 (channels 6-10 may be provided along two axes, a single axis, may follow a straight, curved, separated, or other path through and/or around the pockets 6-20). In one embodiment, channel(s) 6-10 are used for conducting the stimuli. For instance, channels 6-10 may be configured to deliver a cold fluid such as cold air. Channels 6-10 may exhibit good thermal conduction, such that application of cold transfers the cold air to efficiently reach the individual encapsulated solvent pockets 6-20. Channels 6-10 thus route stimuli to the pockets 6-10 more uniformly, providing a more homogenous release across all the pockets 6-10.

The channels 6-10 may also be configured to encourage the stimuli to disrupt the structure. For example, the channels 6-10 may be designed to cause compressed air to expand as it travels through channels 6-10, thereby further reducing the temperature of the air. In other embodiments, the channels 6-10 can be thin solid or hollow metallic bands formed of a material that is a good thermal conductor. Channels 6-10 can also be a material with drastically different or inert thermal responsiveness. In particular, the one or more polymer layers associated with pockets 6-20 can have a high CTE relative to the material comprising the channel 6-10. In other designs, the channel 6-10 may have the higher CTE, whereas the polymer associated with pocket 6-20 may have the lower or otherwise dissimilar CTE.

In still other embodiments, channels 6-10 may be designed to conduct a stimuli such as radiant energy. In those embodiments, channels may be a radio frequency (RF) transmission line or microwave frequency waveguide. Channels 6-10 may thus distribute stimuli in different ways, depending on which stimuli is used.

Figure 7A:
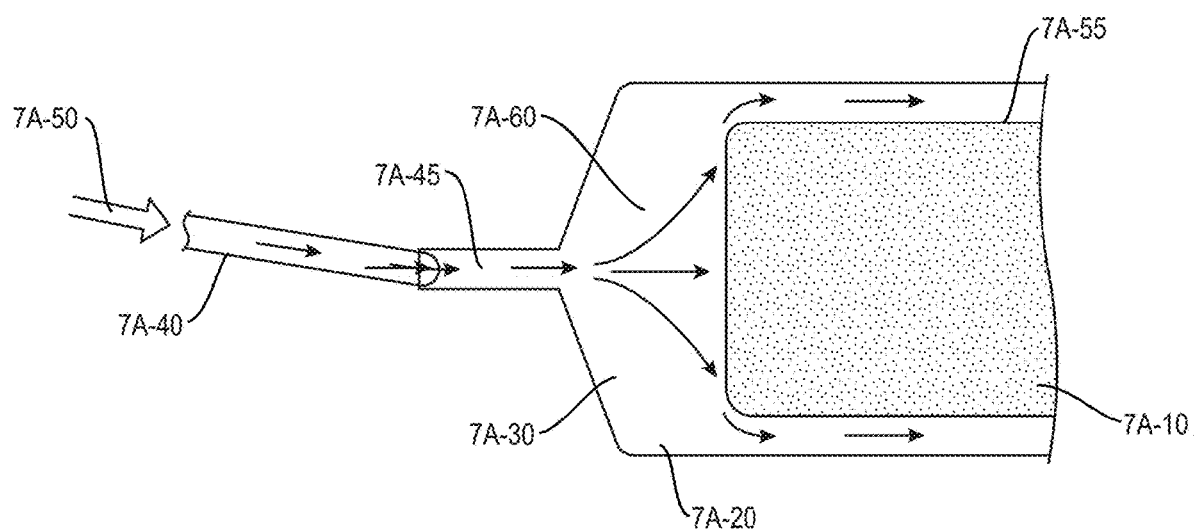
FIG. 7A shows application of compressed air via a nozzle.

FIG. 7A shows an embodiment where a compressed air 7A-50 stimuli is applied via a nozzle 7A-40 which interfaces to a formed opening 7A-45 that feeds a widening channel 7A-30. Channel 7A-30 in turn feeds other channels 7A-20 on either side of solvent pocket 7A-10. Widening channel 7A-30 provides a space for further expansion of the compressed air, which in turn, creates a lower pressure area 7A-60 and a cooling effect to the air flowing in channels 7A-20.

In one embodiment, the cross-sectional area of the widening area 7A-60 is greater than the cross-sectional area of the inlet nozzle 7A-45, thus creating a negative pressure differential to decrease the temperature of the inlet air 7A-50.

As in other embodiments described above, the impact of the cooling fluid flowing from channel 7A-20 encounters the polymer 7A-55 encapsulating the solvent 7A-10 at the boundary between the two. Although not shown in detail in FIG. 7A, that boundary may include an interface of two dissimilar CTE materials, causing disruption and thus release of solvent 7A-10.

Figure 7B:
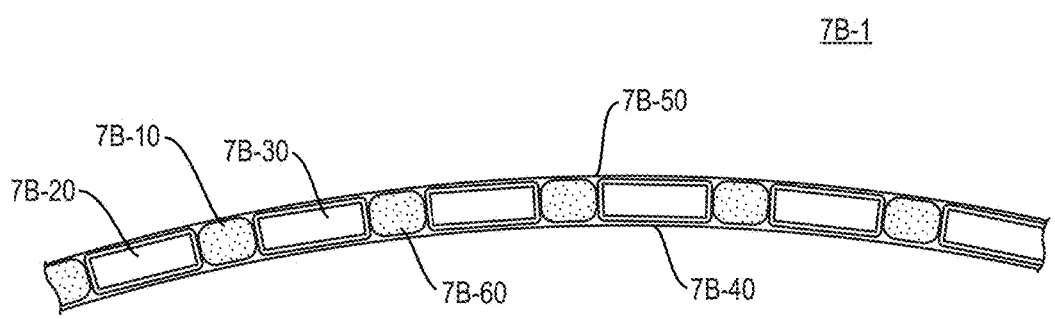
FIG. 7B illustrates another implementation where the structure is formed from alternating adhesive pockets and solvent pockets, some of which may be empty.

FIG. 7B depicts another embodiment of a tape 7B-1 formed from interspersed or alternating solvent pockets. Some of the pockets 7B-20 may be empty and thus serve as channels for distribution of stimuli, for instance, compressed air. Other pockets 7B-30 may be adhesive which is exposed upon removal of protective layer 7B-40. In this embodiment, the encapsulated solvent 7B-10 and empty channels 7B-20 could be alternating. The depicted relative dimensions are for example only, and it may be desirable to have more adhesive 7B-30 pockets and fewer solvent pockets 7B-10 in various proportions. Here 7B-50 depicts a backing layer, which in one embodiment may have a dissimilar CTE relative to the CTE of polymer 7B-60 that encapsulates solvent pockets 7B-10. One or both of these polymers could be stimuli-reactive (in one embodiment, thermoreactive).

Thus it should be understood there are different many geometries possible for arranging the solvent, adhesive, and distribution channels.

The solvent may also be selected to encourage further propagation of the stimulant. For example, the solvent in a given pocket may be such that upon exposure to cold air, causes an endothermic or other reaction that further encourages adjacent pockets to rupture. For example, additives in the encapsulated solvent may, upon release from the pocket, react with other agents so as to cause an endothermic reaction, to propagate the cold (stimuli in this embodiment) as result in adjacent reuptures of other solvent pockets. In some embodiments, a chain reaction may be formed to promote the consistant and rapid release of solvent, once the process has begun. One such endothermic reaction might be ammonium nitrate with water for example. Other such examples might include Ammonium Chloride and/or Potassium Nitrate. In one embodiment Ammonium Chloride might be included in a chamber with solvent, and react with water present in either the adhesive, externally applied with the cold (an ice cube for example), or in a separate chamber which would rupture with the cold as well, and react to create additional cold. Other endothermic reactions may be utilized with an agent in, or near the adhesive reacting with other agents in the solvent in other embodiments.

Other agents, such as cosolvents may also be provided to further this reaction.

Figure 8A:
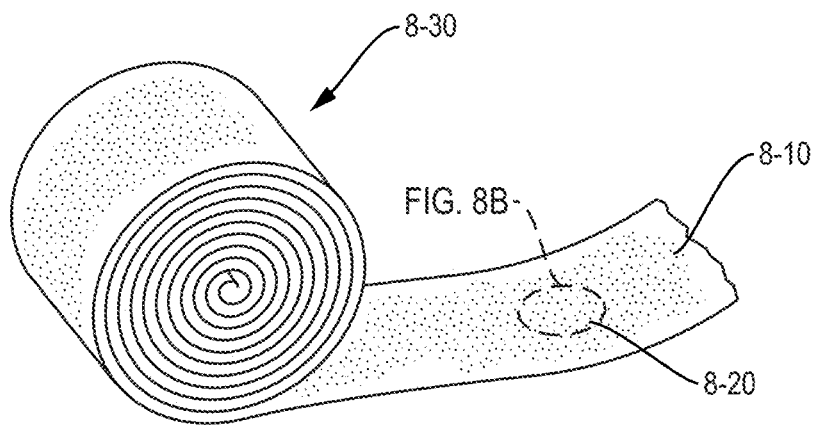
FIGS. 8A and 8B illustrate how various structures may be manufactured as a rolled tape.

FIG. 8A shows how the structures described above may be manufactured as a rolled tape which may be cut and then applied in sections. For instance, such a tape might be used in embodiments such as depicted in FIGS. 1A, 1B, 3 or in other embodiments to be discussed below.

Figure 8B:
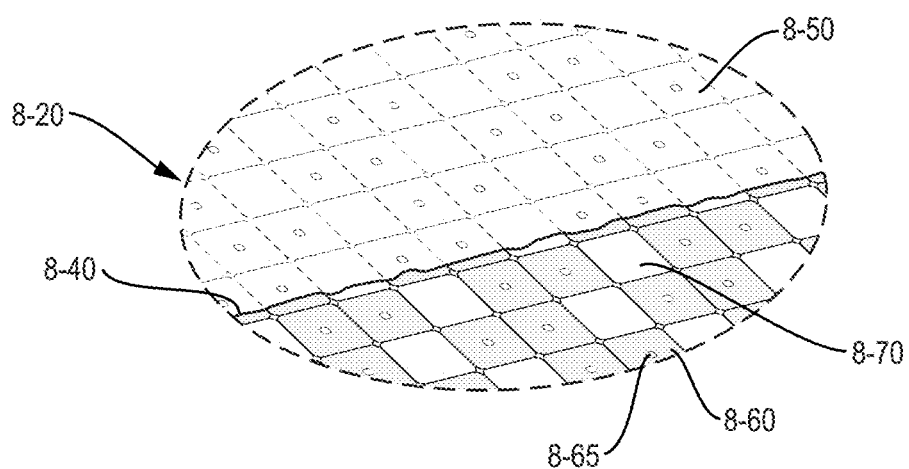

Item 8-80 is a closer view of a circular section 8-20 of the tape 8-30 having a grid structure 8-50. The view of FIG. 8B is a cutaway view taken along line 8-40. Some elements of the grid 8-50, such as item 8-70, are pockets of encapsulated pockets formed on a backing layer 8-50, as in the embodiments described above. Other elements 8-60 have holes 8-65 to allow for access by the stimuli, such as compressed air, that can be exposed to the back of the tape 8-30 when it is to be released.

In some embodiments, the pockets 8-60 that have holes 8-65 would not typically encapsulate solvent directly because the solvent might otherwise leak out. These pockets instead serve to encourage access by the compressed air or other stimuli.

In some configurations, the adhesive may be in a layer below the grid or it may be in the pockets that lack solvent, or in both places.

As with other tapes well known in the art, the adhesive may be exposed when the tape is unrolled. In other implementations, a separate backing layer is peeled away upon use, with the backing layer protecting the adhesive until the tape is ready to be used.

Figure 9:
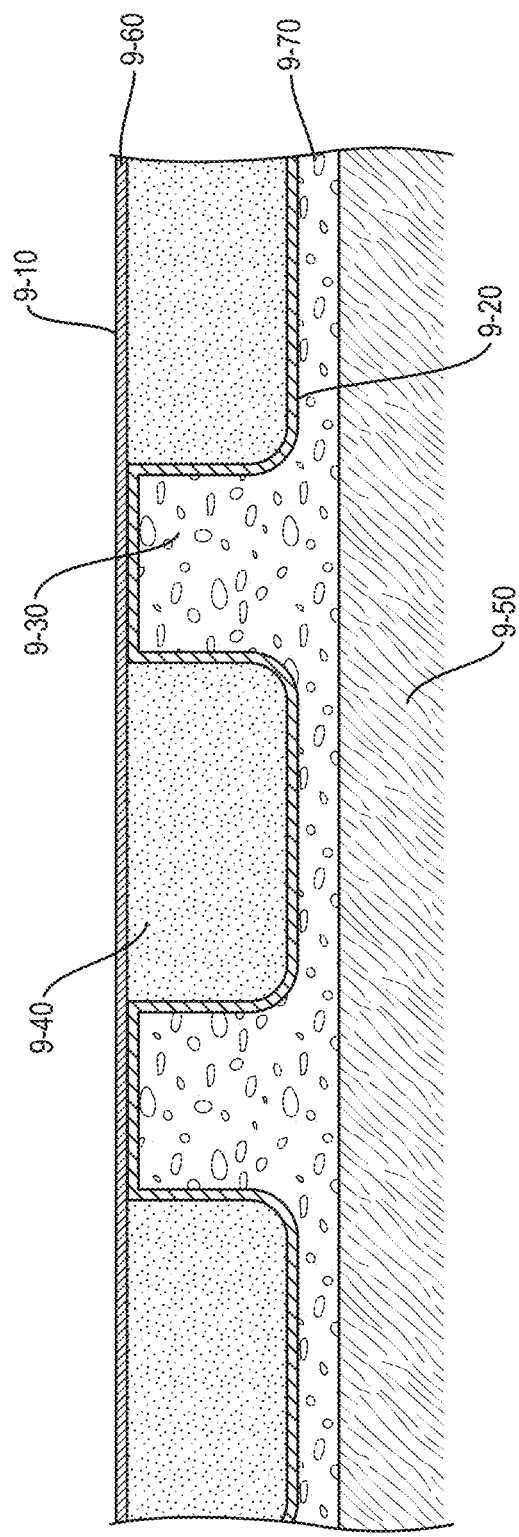
FIG. 9 shows a result with dissimilar coefficient of thermal expansion between two polymer layers.

FIG. 9 depicts another embodiment with adhesive 9-30, a rupturable membrane 9-20 formed of one polymer (in one embodiment, a thermoreactive polymer), backing 9-10, formed of a second polymer having a dissimilar CTE. Adhesive 9-30 covers the space between the solvent pockets 9-40 and is also in a layer 9-70 below the solvent pockets 9-40. The patient's skin or other substrate to what the tape is adhered to is item 9-50.

The basic idea here is to provide adhesive between the solvent pockets 9-40 and the skin 9-50, as well as in the spaces between the solvent pockets 9-40. The advantage of this arrangement is that there is more surface available for adhesive, as well as elimination of the need for a homogenous flat layer with nothing but solvent—thus requiring less solvent. This configuration may also be easier to manufacture. In particular, sonic or thermal welding of the two polymer layers 9-10, 9-20 can be used to construct the article. For example, the top polymer layer 9-10 could be thermally welded to the second polymer layer 9-20 after solvent 9-40 is placed in pockets or depressions formed in second layer 9-20. The adhesive then layered on, to fill both the solvent encapsulation pockets 9-40 as well as below them at 9-70.

Figure 10:
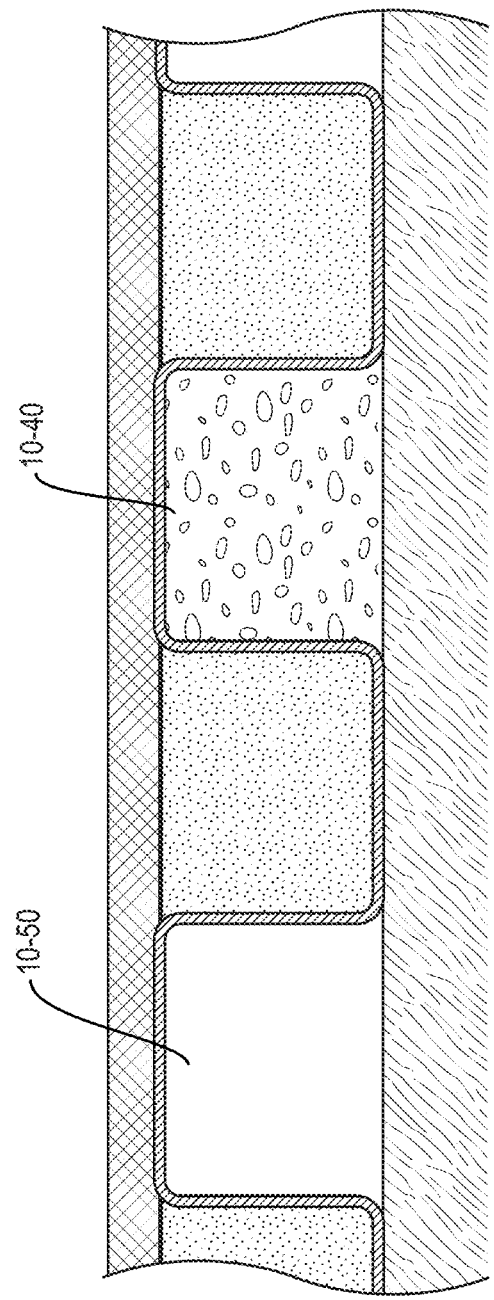
FIG. 10 is another alternative where adhesive is deposited in some areas and not others.

FIG. 10 is a similar but alternative approach where adhesive 10-40 is deposited in only some of the pockets. In this embodiment there is no adhesive in some of the other pockets 10-50, which can instead serve as channels to distribute the stimuli.

In other embodiments, channels 10-50 may be formed of a material such as a metal that heats when stimulated with ultrasonic, radio frequency or microwave energy. In other embodiments channels 10-50 may a fluid other than air, such as water or other media, that expands when exposed to microwave energy. The result is still the same—to cause disruption of one or more polymers to thery expose the solvent to the adhesive.

Figure 11:
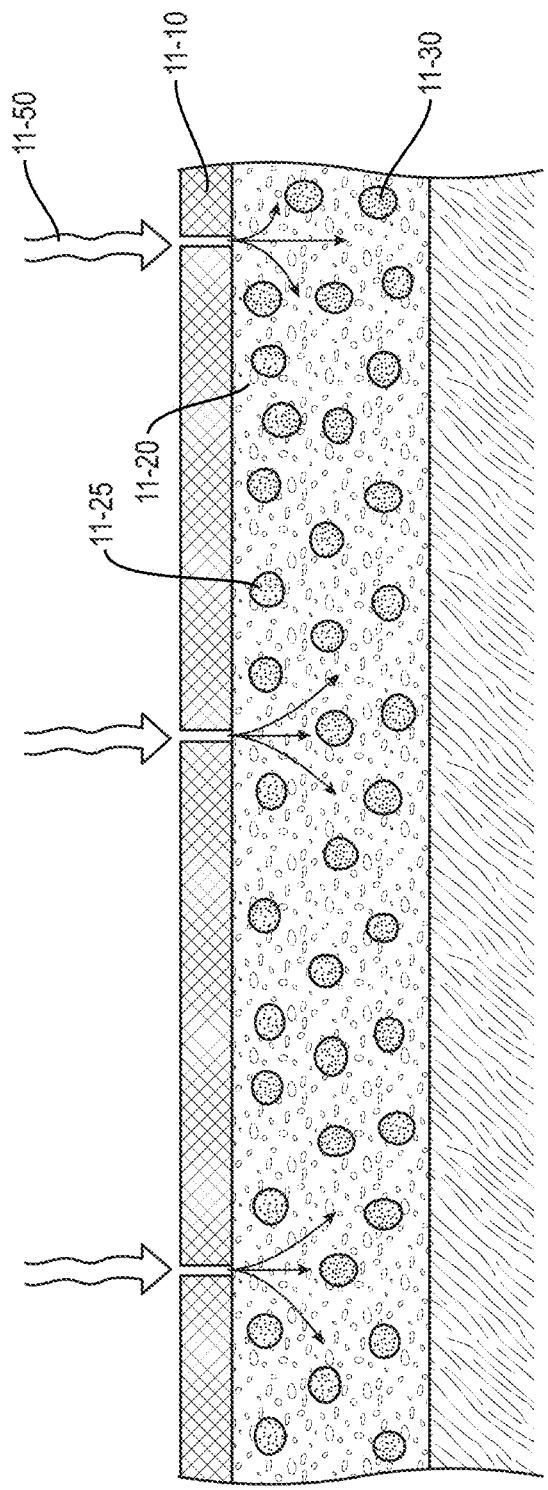
FIG. 11 shows an implementation with polymer spheriods encapsulating the solvent.

FIG. 11 is another alternative where the polymer is shaped as spheroids 11-25 that encapsulate solvent 11-30. The spheroids 11-25 may be suspended in or coated by adhesive 11-20. It may be that the thermal conductivity at the surface of backing layer 11-10 and through adhesive 11-20 is sufficient to rupture the spheres 11-25 when a cold air stimuli is applied to the backing layer 11-10. However, notches 11-50 may be formed in a backing layer 11-10 to serve as channels to further distribute the stimuli 11-50.

The embodiment of FIG. 11 can be manufactured via a particular process. For example, solvent may be forced through a later or suspension of softened polymer. The resulting "bubbles" of polymer then encapsulate the forced solvent as they are cooled. In one embodiment, a warmed solvent and warmed polymer may be placed over a mesh or screen. Pressure then expands the polymer through the mesh and polymer bubbles are formed, which then seal themselves through surface tension on the other side. A cooled solvent layer or other liquid may be disposed on the other side to encourage bubble formation.

When the adhesive layer 11-20 is between about a tenth of a millimeter to one millimeter in thickness, then the spheres 11-25 might have a diameter on the order of a tenth to a fiftieth of that thickness, or about 0.01 to 0.1 millimeters (from 10 to 100 micrometers) in diameter. It should be understood that the geometry of the layers and spheres could be smaller or larger, with the resulting dimensions being generally defined by the size of the mesh used to produce the spheres 11-25.

Figure 12A:
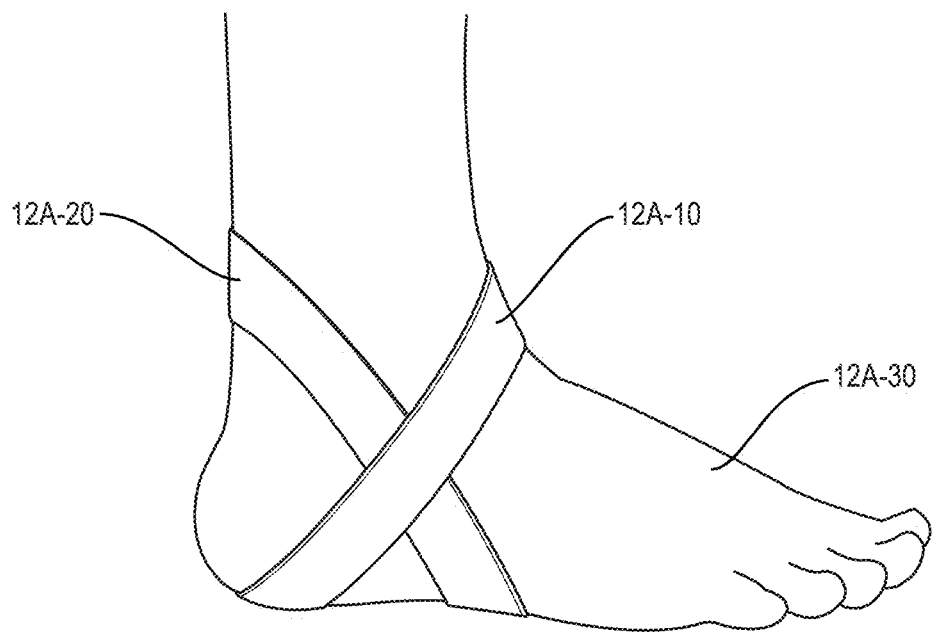
FIG. 12A is an example use case.

FIG. 12A is an example use of the tape 12A-10, 12A-20 in a field application. In this example use case, a first responder is taking care of an injured person at a remote site that is far away from a hospital or other trained medical personnel. The tape may be used by backpackers or soldiers who need an easy to use field dressing. The tape may also be used to apply a splint or even a stabilizing "cast" around a joint such as ankle 12A-30.

Here, a relatively strong adhesive can be used with the tape to provide structural rigidity, because the adhesive will be easily removed when the stimuli is applied at a later time.

Thus, the structure used herein, because of the ability to provide stillness along one or more axes by selective arrangement of the adhesive pockets may serve as kinesiology tapes in the treatment of muscular injuries.

The ability to use a stronger, stiffer adhesive means that the tape can be used in many situations. The tape might be used in place of, for example, a Velcro™ ankle brace. One can thus apply the tape to make a still-flexible ankle brace in the field. Depending on the polymers and adhesives used, the tape can also replace a plaster cast or replace a walking cast to immobilize a damaged muscle, a strained ligament, or tendon, again similar to kinesiology tape but potentially more rigid or semi-rigid.

Figure 12B:
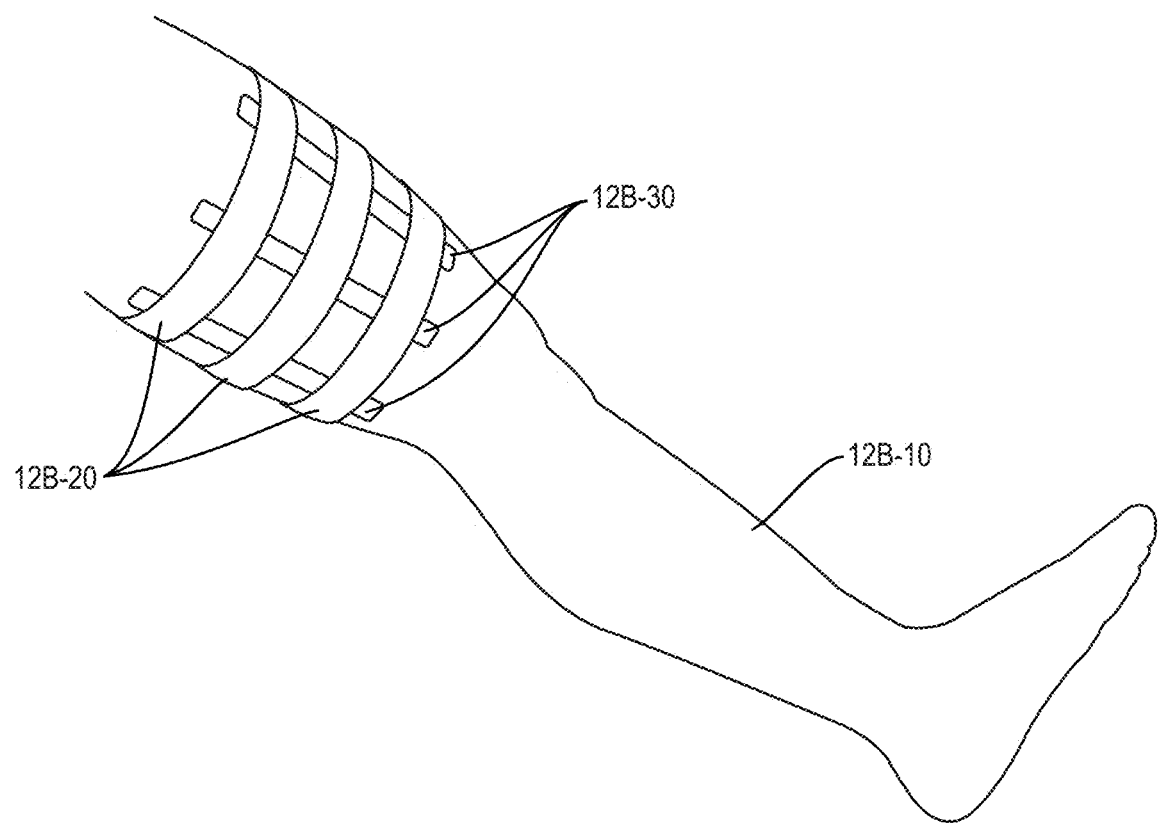
FIG. 12B depicts use of the tape in combination with a splint.

FIG. 12B depicts use of the tape 12B-20 in combination with splints 12B-30 to set a broken femur 12B-10. Splints, sticks, or other stiff object is placed nect to the broken bone and the tape 12B-20 run around them.

Figure 13:
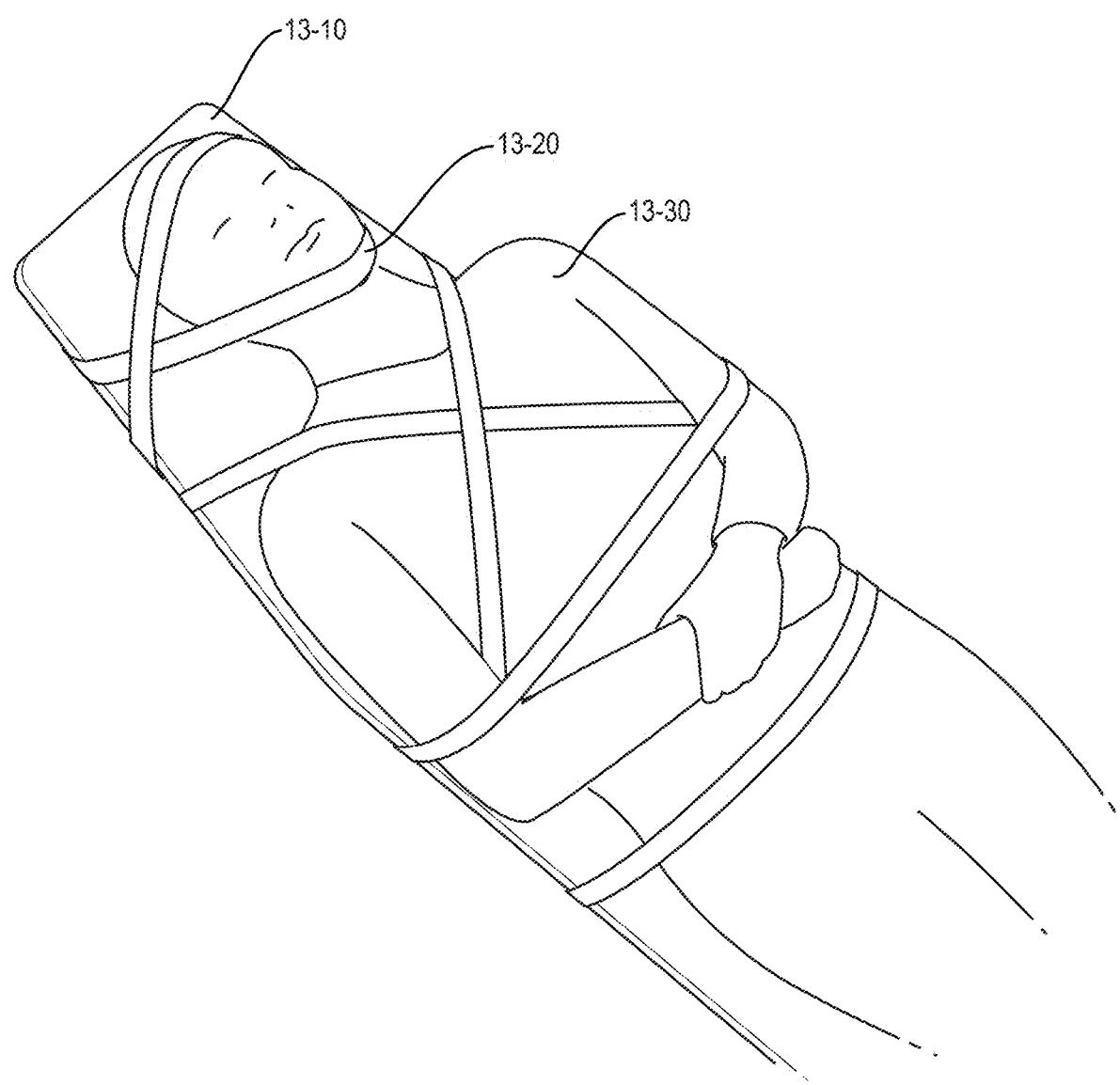
FIG. 13 is another use case where the tape is used to immobilize a patient against a backboard.

FIG. 13 is an embodiment where the tape 13-20 is used to immobilize a patient 13-30 having suffered a very serious neck or back injury in a remote location. The patient is braced on a rigid surface such as a board 13-10. Here the tape can be used to immobilize the patient, with the constraint remaining "permanent" until the stimuli is applied.

Figure 14A:
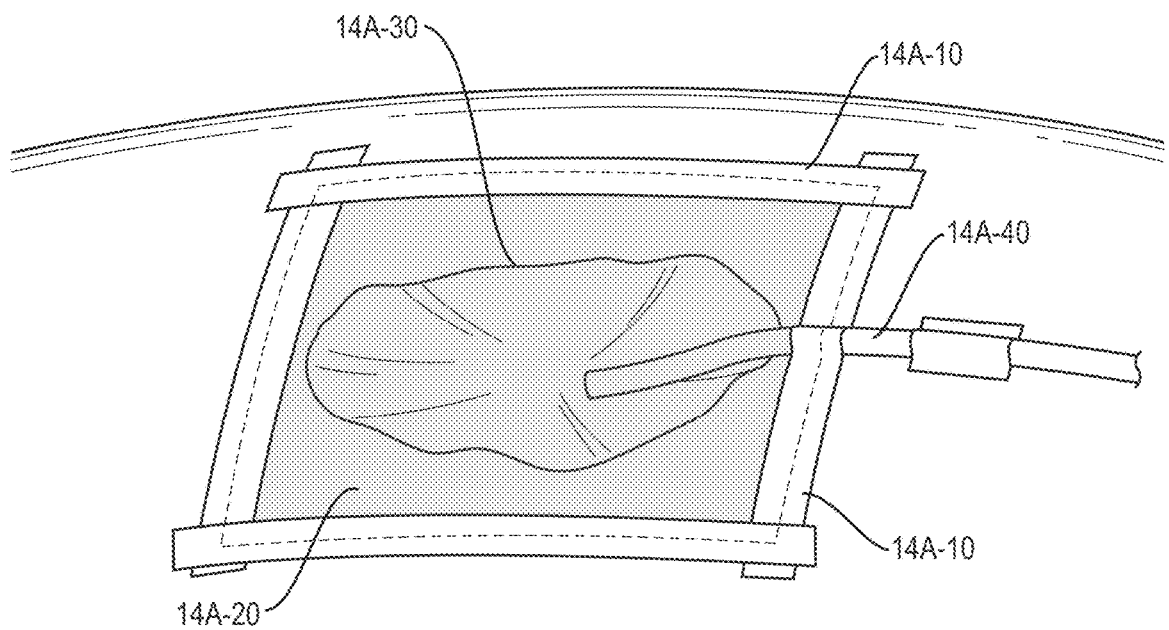
FIG. 14A is a negative pressure wound therapy application.

FIG. 14A is an application of the tape 14A-10 for Negative Pressure Wound Therapy (NPWT). In this embodiment, tape sections 14A-10 secure an NPWT membrane 14A-20. More particularly, a wound 14A-30 is surrounded by the airtight membrane 14A-20, with tape 14A-10 around the edges making a seal. A pump (not shown) produces a slight vacuum for tube 14A-40. Another section of tape 14A-20 may secure the tube 14A-40.

One of the problems currently encountered with NPWT is that if the pressure seal of 14A-20 is lost at any of the interfaces, then the pump will sound an alarm, which nursing staff or a physician must then attend to, by reapplying the tape. There are certain geometries, such as under an armpit, at the bend of an elbow or behind the knee, that are notorious for losing the NPWT seal. These movable joints are very hard to keep sealed with NPWT solutions on the market because the adhesives are typically just standard bandages and they easily come loose with patient movement. Thus a more-aggressive adhesive that won't loosen, even at a joint interface, allows maintaining that seal.

Figure 14B:
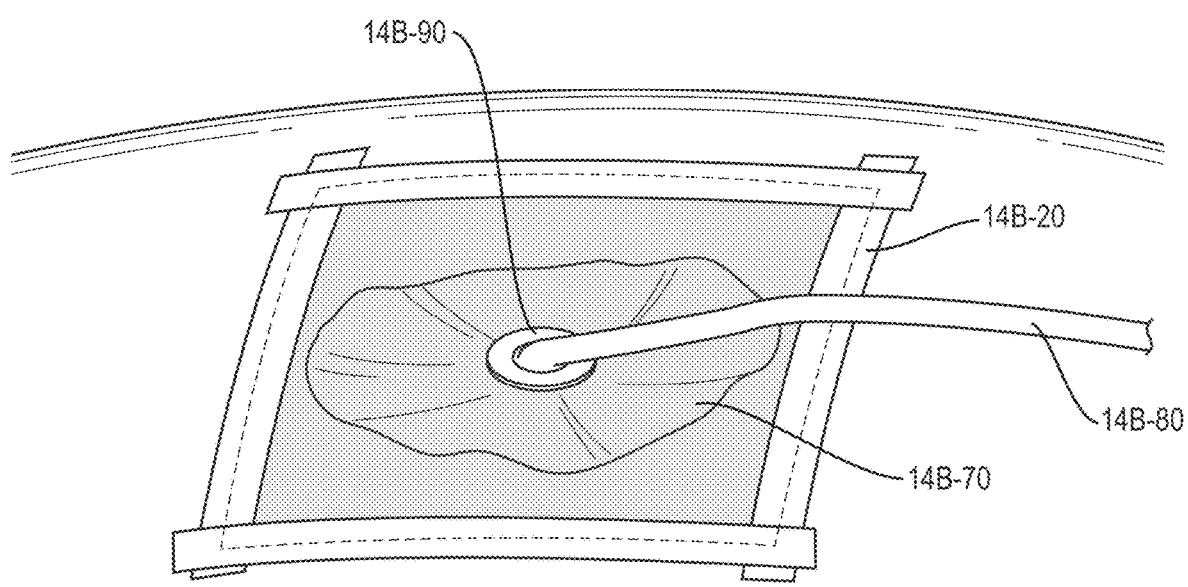
FIG. 14B is another negative wound pressure therapy embodiment.

FIG. 14B shows another NWPT embodiment where the vacuum tube 14B-80 does not run under the tape 14B-20 but rather runs to a surface interfacing to the membrane 14B-60. In this case the surface interface 14B-90 may be a ring that is already bonded to the membrane 14B-70, and thus cannot be released. In this application, the tape 14B-20 is still used to provide an airtight interface between the skin and the membrane 14B-70.

Referring to the adhesive of the stimuli-responsive articles described above, it can be formed of one or more of the following materials: $C_{1-12}$ alkyl acrylate, $C_{1-12}$ alkyl cyanoacrylate, $C_{1-12}$ alkyl methacrylate, $C_{1-12}$ alkyl acrylamide, $C_{1-12}$ alkyl methacrylamide, vinyl ether, vinyl ester, siloxane, hydrogel, hydrocolloid, silicone, silicone gel, and a combination thereof.

In one embodiment, the material for forming the adhesive is $C_{1-12}$ alkyl cyanoacrylate, such as methyl 2-cyanoacrylate, ethyl-2-cyanoacrylate, n-butyl cyanoacrylate, and 2-octyl cyanoacrylate. Preferably, the material of the adhesive of this invention for medical use causes less skin irritation and increases flexibility and strength, as compared to traditional materials. An exemplary material meeting such purpose is n-butyl cyanoacrylate or 2-octyl cyanoacrylate.

Referring to the polymer(s) discussed above, it typically has a glass-transition temperature of –20° C. to 30° C. (e.g., –20° C. to 0° C., –10° C. to 20° C., and 0° C. to 10° C.). The polymer can be a homopolymer or a copolymer.

Examples of the polymer include, but are not limited to, polypropylene, polymethylpentene, poly(3-hydroxybutyrate-co-3-hydroxyvalerate), polyvinylidene chloride, polyethylene, ethylene vinyl alcohol, poly(methyl methacrylate), or polyurethane.

The polymer can also be modified by adding a predetermined amount of additives (e.g., mineral and glass fiber) to form a modified polymer. Examples of the modified polymer include polypropylene 10-40% mineral filled, polypropylene 10-40% talc, and polypropylene 10-20% glass fiber.

In one embodiment, the polymer used in this invention is polypropylene, polymethylpentene, or poly(3-hydroxybutyrate-co-3-hydroxyvalerate).

Referring to the solvent(s) that may be used, it can be a ketone-based solvent, an alcohol-based solvent, or an ester-based solvent. Examples of the solvent include, but are not limited to, acetone, methyl ethyl ketone, isopropanol, ethanol, ethyl acetate, and tetrahydrofurfuryl acetate.

In general, the stimuli-responsive article may have a polymer that is insoluble in the solvent and an adhesive is at least partially soluble or partially swellable in the solvent. Preferably, the adhesive is substantially soluble or substantially swellable in the solvent.

In one embodiment, the polymer, with or without additives, used in the stimuli-responsive article can be resistant to the solvent, i.e., being insoluble, within a certain temperature range, but susceptible to the solvent, i.e., being at least partially soluble or partially swellable, within a different temperature range.

In another embodiment, the stimuli-responsive article can further contain an additive, e.g., a salt, which, upon contacting the solvent, produces a cooling-off effect by absorbing heat. Examples of the salt include, but are not limited to, a sodium salt (e.g., sodium chloride), a calcium salt (e.g., calcium chloride), a magnesium salt (e.g., magnesium chloride), and a potassium salt (e.g., potassium acetate).

In a preferred embodiment, the stimuli-responsive article of this invention includes an adhesive, a polymer defining an enclosed cavity, and a solvent disposed within the cavity, in which the adhesive is formed of methyl 2-cyanoacrylate, ethyl-2-cyanoacrylate, n-butyl cyanoacrylate, or 2-octyl cyanoacrylate, the polymer is polypropylene, polymethylpentene, or poly(3-hydroxybutyrate-co-3-hydroxyvalerate), and the solvent is acetone, methyl ethyl ketone, isopropanol, ethanol, ethyl acetate, or tetrahydrofurfuryl acetate.

An exemplary stimuli-responsive article includes an adhesive formed of n-butyl cyanoacrylate or 2-octyl cyanoacrylate, a polymer of polypropylene or polymethylpentene, and a solvent of acetone or isopropanol.

Thus, it is seen how an adhesive article that is released upon application of stimuli is provided. One skilled in the art will appreciate that this result can be obtained by other than the various embodiments and preferred embodiments, which are presented in this description for purposes of illustration and not of limitation, and the intent is to limit the scope of this patent only by the claims that follow. It is noted that equivalents for the particular embodiments discussed in this description may practice the invention as well.

While various embodiments have been described above, it should be understood that they have been presented by way of example only, and not of limitation. Likewise, the various diagrams may depict an example mechanical, architectural or other configuration, which is done to aid in understanding the structures, features and functionality that may be included. The desired features may be implemented using a variety of alternatives. Indeed, it will be apparent to one of skill in the art how alternative functional, logical or physical partitioning and configurations may be implemented to implement the desired features.

What is claimed is:

1. A stimuli-responsive adhesive article comprising:
   an adhesive,
   a polymer defining an enclosed cavity, and
   a solvent disposed within the cavity,
   whereby the adhesive article is responsive to a stimuli, the stimuli comprising at least one of radiation or temperature change, and, upon application of the stimuli, the adhesive article becomes removable.

2. The article of claim 1, further comprising
   another polymer disposed adjacent said polymer, and wherein the two polymers have different coefficients of thermal expansion.

3. The article of claim 1 wherein the polymer is a polymeric layer on which the adhesive is disposed.

4. The article of claim 1 wherein the polymer defines a spherical enclosed cavity.

5. The article of claim 1 wherein application of the stimuli disrupts the polymer to expose the adhesive to the solvent.

6. The article of claim 2 wherein application of the stimuli further disrupts one or more joints between the two polymers.

7. The article of claim 1 wherein the stimuli comprises one or more of cooling, heating, ultrasonic frequency radiation, radio frequency radiation, or microwave frequency radiation.

8. The article of claim 1 wherein the polymer has a shape defining a plurality of pockets, with the solvent disposed within at least some of the pockets.

9. The article of claim 8 wherein the pockets are aligned in a grid.

10. The article of claim 8 additionally comprising:
one or more channels disposed adjacent the polymer, the channels for conducting the stimuli.

11. The article of claim 10 additionally comprising:
a stimuli inlet portion feeding an expansion space in communication with one or more of the channels.

12. The article of claim 8 additionally comprising:
another polymer disposed adjacent said polymer, and wherein the two polymers are fused together to define the plurality of pockets, and the adhesive is disposed on an outer surface of one of the polymer layers.

13. The article of claim 1 additionally comprising:
a protective layer disposed on the adhesive.

14. The article of claim 1 wherein the polymer defines a plurality of spheroids encapsulating the solvent, and the spheroids are dispersed through the adhesive.

15. The article of claim 1, wherein the polymer is insoluble in the solvent and the adhesive layer is soluble or swellable in the solvent.

16. The article of claim 1, wherein the polymer has a glass-transition temperature ($T_g$) of −20° C. to 30° C.

17. The article of claim 16, wherein the polymer has a $T_g$ of −10° C. to 20° C.

18. The article of claim 17, wherein the polymer has a $T_g$ of 0° C. to 10° C.

19. The article of claim 18, wherein the material is methyl 2-cyanoacrylate, ethyl-2-cyanoacrylate, n-butyl cyanoacrylate, or 2-octyl cyanoacrylate.

20. The article of claim 1, wherein the adhesive contains one or more materials selected from the group consisting of: $C_{1-12}$ alkyl acrylate, $C_{1-12}$ alkyl cyanoacrylate, $C_{1-12}$ alkyl methacrylate, $C_{1-12}$ alkyl acrylamide, and $C_{1-12}$ alkyl methacrylamide.

21. The article of claim 1, wherein the solvent is a ketone-based solvent, an alcohol-based solvent, or an ester-based solvent.

22. The article of claim 21, wherein the solvent is acetone, methyl ethyl ketone, isopropanol, ethanol, ethyl acetate, or tetrahydrofurfuryl acetate.

23. The article of claim 1, wherein the polymer is selected from the group consisting of polypropylene, polymethylpentene, poly(3-hydroxybutyrate-co-3-hydroxyvalerate), polyvinylidene chloride, polyethylene, ethylene vinyl alcohol, poly(methyl methacrylate), and polyurethane.

24. The article claim 23, wherein the polymer is polypropylene, polymethylpentene, or poly(3-hydroxybutyrate-co-3-hydroxyvalerate).

25. The article of claim 23, wherein
the solvent is a ketone-based solvent, an alcohol-based solvent, or an ester-based solvent; and
the adhesive layer contains one or more materials selected from the group consisting of $C_{1-12}$ alkyl acrylate, $C_{1-12}$ alkyl cyanoacrylate, $C_{1-12}$ alkyl methacrylate, $C_{1-12}$ alkyl acrylamide, $C_{1-12}$ alkyl methacrylamide.

26. The article of claim 25, wherein the polymer is polypropylene, polymethylpentene, or poly(3-hydroxybutyrate-co-3-hydroxyvalerate); the solvent is acetone, methyl ethyl ketone, isopropanol, ethanol, ethyl acetate, or tetrahydrofurfuryl acetate; and the adhesive layer is formed of a material selected from the group consisting of methyl 2-cyanoacrylate, ethyl-2-cyanoacrylate, n-butyl cyanoacrylate, and 2-octyl cyanoacrylate.

27. The article of claim 23, wherein the polymer is insoluble in the solvent and the adhesive is soluble or swellable in the solvent; and the polymer has a $T_g$ of −20° C. to 30° C.

28. The article of claim 27, wherein the polymer is polypropylene, polymethylpentene, or poly(3-hydroxybutyrate-co-3-hydroxyvalerate); the solvent is acetone, methyl ethyl ketone, isopropanol, ethanol, ethyl acetate, or tetrahydrofurfuryl acetate; and the adhesive layer is formed of a material selected from the group consisting of methyl 2-cyanoacrylate, ethyl-2-cyanoacrylate, n-butyl cyanoacrylate, and 2-octyl cyanoacrylate.

* * * * *